(12) United States Patent
Hirai et al.

(10) Patent No.: US 8,309,612 B2
(45) Date of Patent: Nov. 13, 2012

(54) METHOD FOR TREATING AGE-RELATED MACULAR DEGENERATION

(75) Inventors: Shin-ichiro Hirai, Ikoma (JP); Atsushi Yoshida, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 188 days.

(21) Appl. No.: 12/451,368

(22) PCT Filed: May 23, 2008

(86) PCT No.: PCT/JP2008/059503
§ 371 (c)(1),
(2), (4) Date: Nov. 9, 2009

(87) PCT Pub. No.: WO2008/146721
PCT Pub. Date: Dec. 4, 2008

(65) Prior Publication Data
US 2010/0120873 A1 May 13, 2010

(30) Foreign Application Priority Data
May 25, 2007 (JP) ................................ 2007-138519

(51) Int. Cl.
*A61K 31/015* (2006.01)
(52) U.S. Cl. ...................................... 514/764; 514/912
(58) Field of Classification Search ................... 514/764, 514/912
See application file for complete search history.

(56) References Cited

U.S. PATENT DOCUMENTS

| | | | |
|---|---|---|---|
| 4,778,814 | A | 10/1988 | Cash |
| 6,342,510 | B1 | 1/2002 | Isakson et al. |
| 6,525,040 | B1 | 2/2003 | Erdelmeier et al. |
| 2002/0037854 | A1 | 3/2002 | Breton et al. |
| 2002/0107276 | A1 | 8/2002 | Isakson et al. |
| 2003/0166632 | A1 | 9/2003 | Ueno |
| 2003/0216290 | A1* | 11/2003 | Lecomte et al. ............ 514/2 |
| 2004/0147581 | A1* | 7/2004 | Taylor et al. ............ 514/406 |
| 2009/0105313 | A1 | 4/2009 | Yoshida et al. |
| 2011/0009376 | A1 | 1/2011 | Hirai et al. |

FOREIGN PATENT DOCUMENTS

| | | |
|---|---|---|
| EP | 02049735 A2 | 12/1987 |
| EP | 02049735 A3 | 12/1987 |
| JP | 2001-261555 A | 9/2001 |
| JP | 2006-104199 A | 4/2006 |
| WO | WO 2004/069157 A | 8/2004 |
| WO | WO 2006/123676 A1 | 11/2006 |

OTHER PUBLICATIONS

Mayo Clinic, Dry Macular Degeneration, Aug. 26, 2010.*
John S. Hurst et al., "Effects of ebselen on arachidonate metabolism by ocular and nonocular tissues", *Biochemical Pharmacology*, vol. 38, No. 19, pp. 3357-3363 ((1989).
Rumi Imaoka et al, "Studies on ocular pharmacology (Rept. 32): Beneficial effect of EPC-K1, a novel antioxidant, on allergic conjunctivitis and peroxynitrite-induced increase in microvascular permeability in guinea pigs", *Japanese Journal of Pharmacology*, vol. 82, No. Suppl. 1, p. 273P (2000).
Teruo Nishida et al, "Clinical classification of the corneal epithelial disorders", *Clinical Opthalmology*, 46, pp. 738-743 (1992) (Abstract on last page).
Chikako Katakami, "A New Treatment for Corneal Epithelial Defects Using Fibronectin, EGF and Hyaluronic Acid", *Ophthalmic Surgery*, 5, pp. 719-727 (1992).
Daniel G. Herrera et al, "Selective impairment of hippocampal neurogenesis by chronic alcoholism: Protective effects of an antioxidant", *Proceeding Natl. Acad. Sci. USA*, 100 (13), pp. 7919-7924 (2003).
J.Z. Nowak, "Age-related macular degeneration (AMD): pathogenesis and therapy," *Pharmacological Reports*, 2006, 58, pp. 353 to 363.
S. Boger et al., "Antioxidants may reduce the risk for age-related maculopathy in populations with high ocular exposure to solar radiation," *Journal of the American Dietetic Association*, 1999, 99(9), Supplement 1, A-45.
F. Bosch-Morell et al., "Efficacy of the antioxidant ebselen in experimental uveitis," *Free Radical Biology & Medicine*, 1999, vol. 27, Nos. 3/4, pp. 388-391.
J.J. Khatri et al., "Vascular Oxidant Stress Enhances Progression and Angiogenesis of Experimental Atheroma," *Circulation*, 2004, 109, pp. 520-525.
T. Tojo et al., "Role of gp91$^{phox}$ (Nox2)-Containing NAD(P)H Oxidase in Angiogenesis in Response to Hindlimb Ischemia," *Circulation*, 2005; vol. 111, pp. 2347-2355.
O. Gealekman et al., "Endothelial dysfunction as a modifier angiogenic response in Zucker diabetic fat rat: Amelioration with Ebselen," *Kidney International*, 2004, vol. 66, pp. 2337-2347.
J. Cai et al., "Oxidative and Protection of the RPE," *Progress in Retinal and Eye Research*, 2000, vol. 19, No. 2, pp. 205-221.
Zhang et al., "Ebselen Suppresses Late Airway Responses and Airway Inflammation in Guinea Pigs," *Free Radical Biology & Medicine*, vol. 32, No. 5, pp. 454-464, 2002.

* cited by examiner

*Primary Examiner* — Zohreh Fay
(74) *Attorney, Agent, or Firm* — Holtz Holtz Goodman & Chick PC

(57) ABSTRACT

An object of the present invention is to find a novel medicinal use of 2-phenyl-1,2-benzisoselenazol-3(2H)-one or a salt thereof. 2-Phenyl-1,2-benzisoselenazol-3(2H)-one or a salt thereof exhibits an excellent inhibitory effect on neovascularization in the choroid and also has a protective effect on retinal pigment epithelial cell damage, and therefore is useful as a prophylactic or therapeutic agent for age-related macular degeneration.

5 Claims, No Drawings

METHOD FOR TREATING AGE-RELATED MACULAR DEGENERATION

This application is the United States national phase application of International Application PCT/JP2008/059503 filed May 23, 2008.

TECHNICAL FIELD

The present invention relates to a prophylactic or therapeutic agent for age-related macular degeneration, containing 2-phenyl-1,2-benzisoselenazol-3(2H)-one or a salt thereof as an active ingredient.

BACKGROUND ART

Age-related macular degeneration (AMD) is one of the leading causes of legal blindness in developed countries at present, and mainly affects the elderly at the age of 50 years or older. AMD is a disease caused by age-related changes in the macula and is broadly classified into exudative and atrophic forms. Exudative AMD is a disease in which new blood vessels from the choroid grow into the macula in the elderly, and hemorrhage or an exudative lesion occurs beneath the retinal pigment epithelium or retina, and eventually scar tissue is formed. Atrophic AMD is a disease associated with atrophy of the macular region or accumulation of drusen. Further, a precursor lesion that leads to the development of exudative and atrophic AMD is particularly called early AMD in some cases, and this lesion is considered to be one pathological condition of AMD.

A basic pathological condition of AMD (particularly exudative AMD) is choroidal neovascularization, which is considered to be developed through age-related changes in macular retinal pigment epithelial cells, Bruch's membrane and choroidal vessels as the cause. However, much of the pathogenic cause and mechanism of choroidal neovascularization has not been elucidated yet and future development is expected.

On the other hand, 2-phenyl-1,2-benzisoselenazol-3(2H)-one (generic name: Ebselen, hereinafter referred to as "Ebselen") has an antioxidative effect and is reported to be useful for cerebral arteriosclerosis and chronic cerebral circulatory insufficiency (Non-patent document 1 and Patent document 1). Further, Ebselen is reported to be useful for a keratoconjunctival disorder such as dry eye or superficial punctate keratopathy (Patent document 2).

As a report of study of the pharmacological effect of Ebselen on neovascularization, Non-patent document 2 reports that Ebselen inhibited ischemia-induced neovascularization in hindlimb tissues of mice, and Non-patent document 3 reports that Ebselen inhibited endogenous hydrogen peroxide-induced carotid artery remodeling and neovascularization in p22phox transgenic mice.

However, these reports show the effect of Ebselen on tissues such as hindlimb blood vessels and carotid arteries. That is, these reports (Non-patent documents 2 and 3) only suggest the effect of Ebselen on other than ocular tissues and do not suggest the pharmacological effect of Ebselen on choroidal neovascularization.

Further, Non-patent document 4 reports the pharmacological effect of Ebselen on neovascularization, however, unlike the previously described reports (Non-patent documents 2 and 3), this document reports that Ebselen ameliorated the progression of microangiopathy and partially restored neovascularization. Specifically, in Non-patent document 4, a study was performed using ZDF (diabetic model) rats, and it is reported that in these models, the renal vascular function was inhibited and the capillary density around the renal tubule was decreased, however, by repeated administration of Ebselen, renal neovascularization was restored. That is, Non-patent document 4 reports the results contradictory to the previously described reports (Non-patent documents 2 and 3) with respect to the pharmacological effect on neovascularization although the study was performed using different model animals, and it does not describe or suggest choroidal neovascularization at all.

As described above, choroidal neovascularization has attracted attention as a basic pathological condition of AMD (particularly exudative AMD), however, much of the mechanism thereof has remained unknown. Further, there is no report of study of the pharmacological effect of Ebselen on choroidal neovascularization, particularly, there is no report of study of the prophylactic and improvement effect of Ebselen on AMD.

On the other hand, it is also known that retinal pigment epithelial cell damage caused by oxidative stress or the like is one of the causes of development or progression of AMD, and its contribution to early and atrophic AMD is considered to be large (Non-patent document 5). Accordingly, protection of retinal pigment epithelial cells against cell damage is considered to be effective as one of the methods for prophylaxis or therapy of AMD (particularly early and atrophic AMD). However, there is no report of study of such a protective effect of Ebselen on cell damage.

Patent document 1: JP-A-2001-261555
Patent document 2: WO 2006/123676
Non-patent document 1: Proc. Natl. Acad. Sci. USA, 100(13), 7919-7924 (2003)
Non-patent document 2: Circulation, 111, 2347-2355 (2005)
Non-patent document 3: Circulation, 109, 520-525 (2004)
Non-patent document 4: Kidney International, 66, 2337-2347 (2004)
Non-patent document 5: Progress in Retinal and Eye Research 19 (2), 205-221, 2000

DISCLOSURE OF THE INVENTION

Problems to be Solved by the Invention

It is an interesting subject to search a new medicinal use of Ebselen.

Means for Solving the Problems

The present inventors made intensive studies to search a new medicinal use of Ebselen and found that Ebselen or a salt thereof has an excellent inhibitory effect on choroidal neovascularization in rat models of laser-induced choroidal neovascularization, and thus the present invention was achieved. That is, Ebselen exhibits a prophylactic or improvement effect on AMD (particularly exudative AMD).

Further, the present inventors found that Ebselen has a protective effect on cell damage in a human retinal pigment epithelial cell line induced by hydrogen peroxide or 4-hydroxynonenal (HNE). That is, Ebselen exhibits a prophylactic or improvement effect on AMD (particularly early and atrophic AMD). On the other hand, quercetin and edaravone generally known to have an antioxidative activity are not found to have such a protective effect on cell damage, and therefore, it is a surprising finding that Ebselen has such an effect as well.

That is, the present invention is directed to a prophylactic or therapeutic agent for AMD comprising Ebselen or a salt thereof as an active ingredient. In particular, the present invention is characterized in that it can be a prophylactic or therapeutic agent for various pathological conditions of AMD, i.e., atrophic and exudative AMD and precursor lesions thereof (early AMD).

Ebselen is a condensed heterocyclic compound represented by the following chemical structural formula [I].

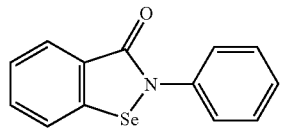

Further, the salt of Ebselen is not particularly limited as long as it is a pharmaceutically acceptable salt, and examples thereof include a salt with an inorganic acid such as hydrochloric acid, nitric acid or sulfuric acid; and a salt with an organic acid such as acetic acid, fumaric acid, maleic acid, succinic acid or tartaric acid. Ebselen may be in the form of a solvate.

In the present invention, AMD includes exudative AMD, atrophic AMD and precursor lesions thereof (early AMD). As described above, AMD is a disease caused by age-related changes in the macula and is broadly classified into exudative and atrophic forms. Exudative AMD is a disease in which new blood vessels from the choroid grow into the macula in the elderly, and hemorrhage or an exudative lesion occurs beneath the retinal pigment epithelium or retina, and eventually scar tissue is formed. Atrophic AMD is a disease associated with atrophy of the macular region or accumulation of drusen.

Ebselen can be formulated into a single preparation or a combination preparation by adding a pharmaceutically acceptable additive as needed using a widely used technique.

When Ebselen is used for prophylaxis or therapy of the above-mentioned eye disease, it can be administered to a patient orally or parenterally. Examples of the route of administration include oral administration, topical administration to eyes (such as instillation administration, administration into conjunctival sac, intravitreal administration, subconjunctival administration and sub-Tenon's administration), intravenous administration and transdermal administration. Further, it is formulated into a dosage form suitable for administration along with a pharmaceutically acceptable additive as needed. Examples of the dosage form suitable for oral administration include tablets, capsules, granules and powders, and examples of the dosage form suitable for parenteral administration include injections, eye drops, ophthalmic ointments, patches, gels and inserts. These can be prepared using a common technique widely used in this field. Further, the present compound can also be formulated into a preparation for intraocular implant or a DDS (drug delivery system) preparation such as a microsphere other than those preparations.

For example, the tablet can be prepared by properly selecting and using an excipient such as lactose, glucose, D-mannitol, anhydrous calcium hydrogen phosphate, starch or sucrose; a disintegrant such as carboxymethyl cellulose, calcium carboxymethyl cellulose, croscarmellose sodium, crosspovidone, starch, partially pregelatinized starch or low-substituted hydroxypropyl cellulose; a binder such as hydroxypropyl cellulose, ethyl cellulose, gum arabic, starch, partially pregelatinized starch, polyvinyl pyrrolidone or polyvinyl alcohol; a lubricant such as magnesium stearate, calcium stearate, talc, hydrous silicon dioxide or a hydrogenated oil; a coating agent such as purified sucrose, hydroxypropylmethyl cellulose, hydroxypropyl cellulose, methyl cellulose, ethyl cellulose or polyvinyl pyrrolidone; a corrigent such as citric acid, aspartame, ascorbic acid or menthol; or the like.

The injection can be prepared by selecting and using a tonicity agent such as sodium chloride; a buffer such as sodium phosphate; a surfactant such as polyoxyethylene sorbitan monoolate; a viscous agent such as methyl cellulose; or the like as needed.

The eye drop can be prepared by selecting and using a tonicity agent such as sodium chloride or concentrated glycerin; a buffer such as sodium phosphate or sodium acetate; a surfactant such as polyoxyethylene sorbitan monooleate, polyoxyl 40 stearate or polyoxyethylene hydrogenated castor oil; a stabilizer such as sodium citrate or sodium edetate; a preservative such as benzalkonium chloride or paraben; or the like as needed. The pH of the eye drop is permitted as long as it falls within the range that is acceptable as an ophthalmic preparation, but is generally preferably in the range of from 4 to 8. Further, the ophthalmic ointment can be prepared with a widely used base such as white petrolatum or liquid paraffin.

The insert can be prepared by pulverizing and mixing a biodegradable polymer such as hydroxypropyl cellulose, hydroxypropylmethyl cellulose, a carboxy vinyl polymer or polyacrylic acid along with the present compound and compression molding the resulting powder. If necessary, an excipient, a binder, a stabilizer or a pH adjusting agent can be used. The preparation for intraocular implant can be prepared using a biodegradable polymer such as polylactic acid, polyglycolic acid, a lactic acid-glycolic acid copolymer or hydroxypropyl cellulose.

The dose of Ebselen can be properly changed depending on the dosage form, severity of symptoms, age or body weight of a patient in need of administration, medical opinion and the like. In the case of oral administration, it can be generally administered to an adult once or divided into several times at a dose of from 0.01 to 5000 mg, preferably from 0.1 to 2500 mg, more preferably from 0.5 to 1000 mg per day. In the case of an injection, it can be generally administered to an adult once or divided into several times at a dose of from 0.0001 to 2000 mg per day. In the case of an eye drop or an insert, generally a preparation containing the active ingredient in an amount of from 0.000001 to 10% (w/v), preferably from 0.00001 to 1% (w/v), more preferably from 0.0001 to 0.1% (w/v) can be administered once or several times per day. Further, in the case of a patch, a patch containing the active ingredient in an amount of from 0.0001 to 2000 mg can be applied to an adult, and in the case of a preparation for intraocular implant, a preparation for intraocular implant containing the active ingredient in an amount of from 0.0001 to 2000 mg can be implanted in an eye of an adult.

Advantageous Effects of the Invention

As will be described below, when the following pharmacological tests were performed, it was shown that Ebselen has an excellent inhibitory effect on choroidal neovascularization in rat models of laser-induced choroidal neovascularization. Further, it was shown that Ebselen also has a protective effect on hydrogen peroxide-induced cell damage and HNE-induced cell damage in a human retinal pigment epithelial cell line. That is, Ebselen is useful as a prophylactic or therapeutic agent for various pathological conditions of AMD.

BEST MODE FOR CARRYING OUT THE INVENTION

Hereinafter, results of pharmacological tests and preparation examples will be shown. However, these examples are for understanding the present invention well, and are not meant to limit the scope of the present invention.

[Pharmacological Test 1]

The usefulness of Ebselen was evaluated using a rat model of laser-induced choroidal neovascularization.

(Production Method for a Rat Model of Krypton Laser-Induced Choroidal Neovascularization)

A rat was given general anesthesia by intramuscular administration of 1 ml/kg of a mixed solution of a 5% (w/v) ketamine hydrochloride injection solution and a 2% xylazine hydrochloride injection solution (7:1), and a 0.5% (w/v) tropicamide-0.5% phenylephrine hydrochloride ophthalmic solution was instilled into the eyes to cause mydriasis, and then, photocoagulation was performed with a krypton laser photocoagulation apparatus. The photocoagulation was performed in a posterior fundus at eight spots per eye sparsely by focusing on the retinal deep layer avoiding thick retinal blood vessels (coagulation conditions: spot size: 100 µm, output: 100 mW, coagulation time: 0.1 sec). After the photocoagulation, the ocular fundus was photographed, and the site where the laser was irradiated was confirmed.

(Drug Administration Method)

Ebselen was suspended in a 1% (w/v) methyl cellulose solution (prepared by dissolving methyl cellulose in purified water) to give a final concentration of 1 mg/ml or 3 mg/ml, and each of the resulting suspensions was orally administered twice daily at a dose of 5 mg/kg or 15 mg/kg (10 mg/kg or 30 mg/kg per day) starting from 5 days before the photocoagulation surgery date for 12 days including the surgery day.

(Evaluation Method)

On day 7 after photocoagulation, each rat was given general anesthesia by intramuscular administration of 1 ml/kg of a mixed solution of a 5% (w/v) ketamine hydrochloride injection solution and a 2% xylazine hydrochloride injection solution (7:1), and a 0.5% (w/v) tropicamide-0.5% phenylephrine hydrochloride ophthalmic solution was instilled into the eyes to cause mydriasis, and then, 0.1 ml of a 10% fluorescein solution was injected into the tail vein, and fluorescence fundus photography was performed. In the fluorescence fundus photography, a spot where fluorescence leakage was not observed (absence of neovascularization) was judged as negative, and a spot where fluorescence leakage was observed was judged as positive. When there are two photocoagulation sites where a little fluorescence leakage was observed, they were judged as positive (presence of neovascularization). The choroidal neovascularization incidence rate (%) was calculated from the number of positive spots relative to the eight laser irradiation spots in accordance with Equation 1, and the inhibition rate (%) of the drug to be evaluated was calculated in accordance with Equation 2. The results of evaluation of Ebselen are shown in Table 1. The case number in each administration group is 8.

Choroidal neovascularization incidence rate(%)=
(Number of positive spots/total number of photocoagulation sites)×100     [Equation 1]

Inhibition rate(%)=$(A0-AX)/A0 \times 100$     [Equation 2]

A0: Choroidal neovascularization incidence rate of vehicle administration group
AX: Choroidal neovascularization incidence rate of drug administration group

TABLE 1

| Group | | Inhibition rate (%) |
|---|---|---|
| Ebselen | each dose: 5 mg/kg, BID | 26.9 |
| | each dose: 15 mg/kg, BID | 28.9 |

(Discussion)

As is apparent from Table 1, it was shown that Ebselen inhibits choroidal neovascularization in the rat models of laser-induced choroidal neovascularization. That is, it was shown that Ebselen has an excellent inhibitory effect on neovascularization in the choroid and has a remarkable prophylactic or improvement effect on AMD (particularly, exudative AMD).

[Pharmacological Test 2]

Oxidative stress causes retinal pigment epithelial dysfunction and is considered to be one of the causes of development or progression of AMD (Proc. Natl. Acad. Sci. USA, 2006; 103: 11282-11287). Therefore, by using ARPE-19 cells (a human retinal pigment epithelial cell line), the protective effect of Ebselen on hydrogen peroxide-induced cell damage was evaluated. In addition, the effects of quercetin and edaravone which are compounds generally known to have an antioxidative activity were also evaluated at the same time, and comparison study was performed.

(Experimental Method)

ARPE-19 cells were seeded in a 96-well plate at $5 \times 10^3$ cells/well and cultured for 24 hours under the conditions of 37° C. in a 5% $CO_2$/95% air atmosphere. As a culture medium for ARPE-19, DMEM/F12 containing 10% fetal bovine serum, 2 mM L-glutamine and 100 U/mL penicillin and 100 µg/mL streptomycin was used. Subsequently, the culture medium was removed and exchanged with a culture medium containing Ebselen, quercetin or edaravone, or a vehicle culture medium. Incidentally, each compound was dissolved in DMSO and diluted to 1000-fold with the culture medium to prepare a culture medium containing each compound at 6.25 µM or 12.5 µM. The vehicle culture medium was prepared by diluting DMSO without containing the compound to 1000-fold with the culture medium. After the cells were cultured for 24 hours under the conditions of 37° C. in a 5% $CO_2$/95% air atmosphere, the culture medium was removed and exchanged with a culture medium containing hydrogen peroxide (250 µM). After the cells were further cultured for 24 hours under the above-mentioned conditions, the cell viability was measured. In the measurement, Cell Counting Kit-8 (Dojin Kagaku) was used.

(Evaluation Method)

The mean±the standard error (%) of the cell viability of each compound-treated group was expressed by taking the mean value of the cell viability of the untreated cells as 100%. The case number in each group is 4.

(Results)

The protective effect of each compound on hydrogen peroxide-induced cell damage is shown in Table 2. The cell viability of ARPE-19 cells treated with hydrogen peroxide was decreased to 7.2% of that of the untreated case. As is apparent from Table 2, Ebselen strongly protected the cells against hydrogen peroxide-induced cell damage in a concentration-dependent manner, and particularly at 12.5 µM, Ebselen increased the cell viability to 82.6%. On the other hand, quercetin and edaravone were not found to have a cell protective effect at either concentration.

TABLE 2

| Compound | Concentration of compound (μM) | Cell viability (%) |
| --- | --- | --- |
| Vehicle culture medium | — | 7.2 ± 0.7 |
| Ebselen | 6.25 | 27.1 ± 1.7 |
| Ebselen | 12.5 | 82.6 ± 5.4 |
| Quercetin | 6.25 | 8.0 ± 0.1 |
| Quercetin | 12.5 | 3.8 ± 0.4 |
| Edaravone | 6.25 | 7.7 ± 0.7 |
| Edaravone | 12.5 | 7.5 ± 0.7 |

(Discussion)

From the above results, it was revealed that Ebselen exhibits a strong protective effect on retinal pigment epithelial cell damage induced by hydrogen peroxide. On the other hand, in view of the fact that other compounds having an antioxidative activity do not exhibit the effect, it is a surprising finding that Ebselen has such a protective effect on cell damage as well. That is, it was shown that Ebselen has a prophylactic or improvement effect on AMD (particularly early and atrophic AMD).

[Pharmacological Test 3]

It is known that reactive oxygen species promote membrane lipid peroxidation, resulting in production of HNE (Exp. Eye. Res., 2006; 83: 165-175). HNE forms a covalent bond with a cysteine, lysine or histidine side chain of a protein and inhibits the normal function of the protein, and therefore has a high cytotoxic activity (Invest. Opthalmol. Vis. Sci. 2007; 48: 3469-3479). It is reported that an HNE-modified protein is present also in drusen beneath the retina which is considered to be a deposit inducing AMD, and it is considered to cause retinal pigment epithelial cell damage and also considered to be one of the causes of development or progression of a disease attributed to retinal pigment epithelial damage (Mol. Vis., 2005; 11: 1122-1134, Invest. Opthalmol. Vis. Sci., 2003; 44: 3663-3668, FEBS Lett., 2002; 528: 217-221). Therefore, by using ARPE-19 cells, the protective effect of Ebselen on HNE-induced cell damage was evaluated. In addition, the effects of quercetin and edaravone which are compounds generally known to have an antioxidative activity were also evaluated at the same time, and comparison study was performed.

(Experimental Method)

ARPE-19 cells were seeded in a 96-well plate at 5×10$^3$ cells/well and cultured for 24 hours under the conditions of 37° C. in a 5% $CO_2$/95% air atmosphere. As a culture medium for ARPE-19, DMEM/F12 containing 10% fetal bovine serum, 2 mM L-glutamine and 100 U/mL penicillin and 100 μg/mL streptomycin was used. Subsequently, the culture medium was removed and exchanged with a culture medium containing Ebselen, quercetin or edaravone, or a vehicle culture medium. Incidentally, each compound was dissolved in DMSO and diluted to 1000-fold with the culture medium to prepare a culture medium containing each compound at 12.5 μM. The vehicle culture medium was prepared by diluting DMSO without containing the compound to 1000-fold with the culture medium. After the cells were cultured for 24 hours under the conditions of 37° C. in a 5% $CO_2$/95% air atmosphere, the culture medium was removed and exchanged with a culture medium containing HNE (100 μM). After the cells were further cultured for 24 hours under the above-mentioned conditions, the cell viability was measured. In the measurement, Cell Counting Kit-8 (Dojin Kagaku) was used.

(Evaluation Method)

The mean±the standard error (%) of the cell viability of each compound-treated group was expressed by taking the mean value of the cell viability of the untreated cells as 100%. The case number in each group is 4.

(Results)

The cell protective effect of each compound on HNE-induced cell damage is shown in Table 3. The cell viability of ARPE-19 cells treated with HNE was decreased to 21.9% of that of the untreated case. As is apparent from Table 3, Ebselen strongly protected the cells against HNE-induced cell damage and increased the cell viability to 92.9%. On the other hand, quercetin and edaravone were not found to have a cell protective effect.

TABLE 3

| Compound | Concentration of compound (μM) | Cell viability (%) |
| --- | --- | --- |
| Vehicle culture medium | — | 21.9 ± 2.0 |
| Ebselen | 12.5 | 92.9 ± 2.2 |
| Quercetin | 12.5 | 28.6 ± 0.9 |
| Edaravone | 12.5 | 24.5 ± 1.1 |

(Discussion)

From the above results, it was revealed that Ebselen exhibits a strong protective effect on retinal pigment epithelial cell damage induced by HNE. On the other hand, in view of the fact that other compounds having an antioxidative activity do not exhibit the effect, it is a surprising finding that Ebselen has such a protective effect on cell damage as well. That is, it was shown that Ebselen has a prophylactic or improvement effect on AMD (particularly early and atrophic AMD).

[Pharmacological Test 4]

A light damage model is an animal model in which damage has been induced by light irradiation mainly in the photoreceptor cells and retinal pigment epithelial cell layer and is widely used mainly as an animal model of retinal degeneration (for example, AMD, particularly atrophic AMD or retinitis pigmentosa) (Invest. Opthalmol. Vis. Sci., 2005; 46: 979-987).

(Production Method for a Rat Model of Light Damage)

After a 0.5% (w/v) tropicamide-0.5% phenylephrine hydrochloride ophthalmic solution is instilled into the eyes of a rat to cause mydriasis, light irradiation (for example, illuminance: 2000 Lux, irradiation time: 48 hours) is performed with an apparatus for inducing light damage thereby inducing light damage.

(Evaluation Method)

Ebselen is dissolved in a suitable vehicle and administered to each rat before light irradiation. After light irradiation is completed, 4-hour dark adaptation is performed in a dark room. The rat is given general anesthesia by intramuscular administration of 1 ml/kg of a mixed solution of a 5% (w/v) ketamine hydrochloride injection solution and a 2% xylazine hydrochloride injection solution (7:1), and a 0.5% (w/v) tropicamide-0.5% phenylephrine hydrochloride ophthalmic solution is instilled into the eyes to cause mydriasis. Then, the electroretinogram (ERG) is measured and a- and b-wave amplitudes are calculated from the obtained waveforms. By calculating the inhibition rate (%) of Ebselen against the decrease in the amplitudes of a- and b-waves (photoreceptor cell damage) caused by light irradiation, the prophylactic or improvement effect of Ebselen on AMD (particularly atrophic AMD) can be evaluated. Further, by using the eye after ERG measurement, the number of nuclei in the outer nuclear layer is pathologically counted. By also calculating the inhibition rate (%) of Ebselen against the decrease in the number of nuclei in the outer nuclear layer by light irradiation, the prophylactic or improvement effect of Ebselen on AMD (particularly atrophic AMD) can be similarly evaluated.

PREPARATION EXAMPLES

The pharmaceuticals of the invention will be more specifically described with reference to preparation examples, however, the invention is not limited only to these preparation examples.

Formulation Example 1

Eye Drop in 100 ml

| Ebselen | 10 mg |
|---|---|
| Sodium chloride | 900 mg |
| Polysorbate 80 | q.s. |
| Disodium hydrogen phosphate | q.s. |
| Sodium dihydrogen phosphate | q.s. |
| Sterile purified water | q.s. |

Ebselen and the other above-mentioned ingredients are added to sterile purified water, and these ingredients are mixed well, whereby an eye drop is prepared. By changing the addition amount of Ebselen, an eye drop containing Ebselen at a concentration of 0.05% (w/v), 0.1% (w/v), 0.5% (w/v) or 1% (w/v) can be prepared.

Formulation Example 2

Ophthalmic Ointment in 100 g

| Ebselen | 0.3 g |
|---|---|
| Liquid paraffin | 10.0 g |
| White petrolatum | q.s. |

Ebselen is added to uniformly melted white petrolatum and liquid paraffin, these ingredients are mixed well, and the resulting mixture is gradually cooled, whereby an ophthalmic ointment is prepared. By changing the addition amount of Ebselen, an ophthalmic ointment containing Ebselen at a concentration of 0.05% (w/w), 0.1% (w/w), 0.5% (w/w), 1% (w/w) or 3% (w/w) can be prepared.

Formulation Example 3

Tablet in 100 mg

| Ebselen | 1 mg |
|---|---|
| Lactose | 66.4 mg |
| Cornstarch | 20 mg |
| calcium Carxboxymethyl cellulose | 6 mg |
| Hydroxypropyl cellulose | 6 mg |
| Magnesium stearate | 0.6 mg |

Ebselen and lactose are mixed in a mixer, calcium carboxymethyl cellulose and hydroxypropyl cellulose are added thereto, and the resulting mixture is granulated. The obtained granules are dried, followed by sizing. Then, magnesium stearate is added and mixed with the sized granules and the resulting mixture is tableted with a tableting machine. By changing the addition amount of Ebselen, a tablet containing Ebselen in an amount of 0.1 mg, 10 mg or 50 mg in 100 mg of tablet can be prepared.

Preparation Example 4

Injection in 10 ml

| Ebselen | 10 mg |
|---|---|
| Sodium chloride | 90 mg |
| Polysorbate 80 | q.s. |
| Sterile purified water | q.s. |

Ebselen and sodium chloride are dissolved in sterile purified water, whereby an injection is prepared. By changing the addition amount of Ebselen, an injection containing Ebselen in an amount of 0.1 mg, 10 mg or 50 mg in 10 ml of injection can be prepared.

INDUSTRIAL APPLICABILITY

Ebselen has an excellent inhibitory effect on choroidal neovascularization and also has a protective effect on hydrogen peroxide-induced cell damage and HNE-induced cell damage in a human retinal pigment epithelial cell line. Accordingly, Ebselen is useful as a prophylactic or therapeutic agent for various pathological conditions of age-related macular degeneration.

The invention claimed is:

1. A method for treating age-related macular degeneration consisting of administering a composition comprising a pharmacologically effective amount of 2-phenyl-1,2-benzisoselenazol-3(2H)-one or a salt thereof as a sole active ingredient and a pharmacologically acceptable carrier to a patient in need thereof.

2. A method for treating age-related macular degeneration consisting of administering a composition comprising a pharmacologically effective amount of 2-phenyl-1,2-benzisoselenazol-3(2H)-one or a salt thereof as a sole active ingredient and a pharmacologically acceptable carrier to a patient in need thereof by instillation administration, intravitreal administration, subconjunctival administration, administration into the conjunctival sac, sub-Tenon's administration or oral administration.

3. A method for treating age-related macular degeneration consisting of administering an eye drop, an ophthalmic ointment, an insert, a patch, an injection, a tablet, a fine granule or a capsule containing a pharmacologically effective amount of 2-phenyl-1,2-benzisoselenazol-3(2H)-one or a salt thereof as a sole active ingredient and a pharmacologically acceptable carrier to a patient in need thereof.

4. The method according to any one of claims 1, 2 or 3, wherein the age-related macular degeneration is exudative age-related macular degeneration.

5. The method according to any one of claim 1, 2 or 3, wherein the age-related macular degeneration is atrophic or early age-related macular degeneration.

* * * * *